United States Patent [19]

Kisfaludy et al.

[11] 4,209,442
[45] Jun. 24, 1980

[54] ANGIOTENSIN II ANALOGS AND PROCESS FOR THE PREPARATION THEREOF

[75] Inventors: Lajos Kisfaludy; Györgyne Nyéki nee Olga Kuprina; Lászlóné Szirmai nee Maria Sarközi; Egon Kárpáti; Katalin Gidai; Laszlo Szporny, all of Budapest, Hungary

[73] Assignee: Richter Gedeon Vegyeszeti Gyar Rt., Budapest, Hungary

[21] Appl. No.: 923,663

[22] Filed: Jul. 11, 1978

[30] Foreign Application Priority Data

Jul. 18, 1977 [HU] Hungary ............................. RI 641

[51] Int. Cl.² .................... C07C 103/52; A61K 37/00
[52] U.S. Cl. ............................... 260/112.5 R; 424/177
[58] Field of Search .................. 260/112.5 R; 424/177

[56] References Cited

U.S. PATENT DOCUMENTS

| 3,886,134 | 5/1975 | Sipos et al. | 260/112.5 R |
| 3,920,627 | 11/1975 | Wissmann et al. | 260/112.5 R |
| 3,923,771 | 12/1975 | Bumpus et al. | 260/112.5 R |

Primary Examiner—Delbert R. Phillips
Attorney, Agent, or Firm—Karl F. Ross

[57] ABSTRACT

Novel Angiotensin II peptides of the formula:

X-Arg-Val-Tyr-Ile-His-Pio-Y where X is hydroxyacetyl or α-hydroxypropyl and Y is leucyl, isoleucyl, alanyl or threonyl or an acid addition salt or a complex thereof are disclosed and a process for the preparation thereof are disclosed having the ability to lower renal hypertension.

7 Claims, No Drawings

ANGIOTENSIN II ANALOGS AND PROCESS FOR THE PREPARATION THEREOF

The invention relates to new angiotensin II analogs possessing antagonistic properties, as well as to a process for the preparation of same.

The new angiotensin II peptides are encompassed by the formula I

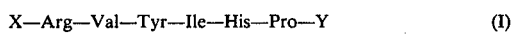

X—Arg—Val—Tyr—Ile—His—Pro—Y    (I)

wherein

X is a radical derived from an aliphatic α-hydroxycarboxylic acid and

Y is a radical derived from an aliphatic α-amino carboxylic acid.

The preferred representatives of the radicals derived from an aliphatic α-hydroxy-carboxylic acid represented by X are hydroxyacetyl and α-hydroxypropionyl groups, while Y preferably represents a leucyl, isoleucyl, alanyl or threonyl group.

Acid-addition salts and complexes of the peptides having the formula I are also within the scope of this invention.

Angiotensin II is an octapeptide having a hypertensive activity. In the organism angiotensin I is prepared from α-globulin produced by the liver by means of an enzyme called resin, liberated from the kidney. In the organism this compound is converted into angiotensin II.

The first angiotensin II analogue was reported for the first time in 1970. It was found that this compound acted as a specific competitive inhibitor of angiotensin II in in vivo and in vitro tests (G. R. Marshall et al: Proc. Natl. Acad. Sci. USA 67, 1624 (1970); P. A. Khairallah et al.: J. Med. Chem. 13, 181 (1970). This observation has brought about a wide-spread interest and stimulated numerous laboratories to synthesize and observe new angiotensin II analogs, which possess antagonistic properties and thus may be used to diagnose or even treat hypertension depending on renin. It turned out already at the very beginning of the research work that analogs, in which the 8-Phe group was substituted by an amino acid having an aliphatic side-chain, were the most promising compounds for this purpose. This change in the structure of the angiotensin II molecule means practically the disappearence of agonistic activity and the appearance of the strong antagonistic activity (D. Gagnon et al.: Br. J. Pharmacol., 43, 409 (1971); D. T. Pals et al.: Circ. Res., 29, 664 (1971)). The antagonistic activity can considerably be increased, when—in addition to the modification carried out in the 8-position—the 1-Asp group is replaced by a Sar group (D. T. Pals et al.: Circ. Res., 29, 673 (1971)). (Sar[1], Ala[8])-Angiotensin II prepared in this way has already been put in circulation. The advantageous properties of this compound are attributed to a decrease in the in vivo enzymatic decomposition and to its great affinity to the receptor sites.

The assumption that antagonistic analogues of angiotensin II can find application in diagnosis and, in some instances, in the treatment of hypertension depending on renin (D. Ganten and F. Gross: Med. Klin. 71, 2043 (1976); J. L. Marx: Science 194, 821 (1976); P. Needleman and G. R. Marshall: Fed. Proc. 35, 2486 (1976)) has been proved by clinical tests (H. R. Brunner et al.: Lancet, 1045 (1973)); A. J. M. Donker et al.: Lancet, 1535 (1974); T. Ogihara et al.: Lancet, 219 (1974); J. H. Laragh et al.: New Engl. J. Med., 292, 695 (1975); W. A. Pettinger et al.: New Engl. J. Med., 292, 1214 (1975); D. H. P. Streeten et al.: Circ. Res. 36, Suppl. 1., 125 (1975); H. R. Brunner and H. Gavras: Schweitz, med. Wschr. 106, 1791 (1976)).

The comparison of the sturcture and biological activity of angiotensin II analogs prepared previously has furnished some very important information for the interpretation of agonistic-antagonistic activity (M. C. Khosla et al.: "Handbook of Experimental Pharmacology" vol 37, I. H. Page and F. H. Bumpus eds. 1974; G. R. Marshall: Fed. Proc., 35, 2494 (1976)).

In the center of the present research work there is the preparation of new antagonists devoid of undesired side-effects and possessing a longer biological half-period (M. C. Khosla et al.: J. Med. Chem., 19, 244 (1976); ibid., 20, 253 (1977)).

It has now been found that replacing the 8-phenylalanine moiety in the molecule of angiotensin II by an aliphatic α-amino-carboxylic acid radical and simultaneously attaching an aliphatic α-hydroxy-carboxylic acid radical to the 1-position yield new angiotensin II competitive inhibitors which considerably decrease hypertension induced by angiotensin II in in vivo tests even in the case of subcutaneous administration.

According to the invention compounds of the formula I

X—Arg—Val—Tyr—Ile—His—Pro—Y    (I)

wherein X and Y are as defined above, are prepared by reacting a reactive heptapeptide derivative having the formula II

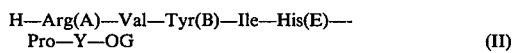

H—Arg(A)—Val—Tyr(B)—Ile—His(E)—Pro—Y—OG    (II)

wherein

A is a group suitable for a temporary protection of the guanidino group of Arg;

B is a group suitable for a temporary protection of the aromatic hydroxyl group of Tyr, E is a group suitable for a temporary protection of the imidazolo group of His and G is a group suitable for the protection of the carboxyl group of C-terminal aliphatic amino acid, which protecting group is stable under mild acid conditions but can be split off by means of strong acids or bases or by catalytic hydrogenation and Y is as defined above, with a reactive aminooxycarboxylic acid derivative of the formula III

W—X'—M    (III)

wherein

X' is a group derived from an α-aminooxiacetyl aliphatic carboxylic acid,

W is a protecting group removable by acidolysis or catalytic hydrogenation,

M is a hydroxyl group or an activating group splitting off the protecting group E and subsequently the other side-chain and terminal protecting groups from the compounds of the formula IV obtained

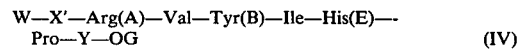

W—X'—Arg(A)—Val—Tyr(B)—Ile—His(E)—Pro—Y—OG    (IV)

wherein

B, W, X', Y, A, E and G are as defined above, the latter one by catalytic hydrogenation, and, if desired, converting a compound of the general formula I obtained into an acid addition salt or a complex thereof.

In the compounds of the formula III A preferably represents a nitro or tesyl group; B preferably is a benzyl or substituted benzyl group; and E preferably is a dinitrophenyl group. In the starting compounds having the formula III W preferably stands for a benzyloxycarbonyl or for a tert.-butyloxycarbonyl group, X' preferably means an aminooxyacetyl or α-aminooxypropionyl group and M preferably represents a pivaloyloxy, nitrophenoxy, pentafluorophenoxy, N-succinimidoxy azido, 2,3,5-trichlorophenoxy or pentachlorphenoxy group.

The protecting group E is preferably split off by means of 2-mercaptoethanol while the remaining side-chain and terminal protecting groups are eliminated by catalytic hydrogenation. This also means that all the side-chain and terminal protecting groups—apart from the protecting group E—can be eliminated in a single reaction step. As a result of the removal of an amino group from the N-terminal α-aminooxy acid in the form of ammonia an α-hydroxy-acid is obtained. This elimination of the α-hydroxy-acid group is reported herein for the first time.

The reactive heptapeptide derivatives of the formula II used as starting materials in the synthesis of the compounds of this invention can be prepared by any method known in the chemistry of peptides. An appropriate method is described for example in the Hungarian Patent Specification No. 168,431. According to this method the functional groups of the side-chains are protected by groups which are stable under the condition of acydolysis carried out when eliminating the protecting group after coupling.

According to a preferred embodiment of the process according to the invention for the temporary protection of the carboxylic group of the C-terminal amino acid, a p-nitrobenzyl group (NB) is used, the guanilino group of arginine is protected by a nitro group, while the hydroxyl group of tirosine is protective with a benzyl group (Bzl) and the protecting group of the imidazole ring of histidine is a dinitrophenyl group (Dnp). All these protecting groups are stable under mild acid conditions. Consequently the N-terminal t-butoxycarbonyl group (Boc) can be eliminated without any risk of splitting off these groups. This special combination of protecting groups enables us to eliminate dinitrophenyl group in the first place and subsequently preparing compounds of the formula I in a single reaction step, by catalytic hydrogenation.

Compounds of the formula I can be purified in a manner known per se, preferably by a carboxymethylcellulose ion-exchanger chromatography. As a result of this technology compounds are generally obtained as lyophilized powders which can easily be transformed into various salts or complexes.

The antagonistic activity of the compounds having the formula I was tested on tomcats. The blood pressure was measured on the cervical artery. The tests were performed by introducing a Hypertension (CIBA) infusion into a lateral femoral vane at a speed of 0.5 μg/kg/min. When the increase in blood pressure was stabilized, the aqueous, physiological or carrier-containing solutions of the test compounds and Saralasin were administered in a single dose, intravenously or subcutaneously, and the decrease in blood pressure was measured.

In the Table 1 the decrease in the arterial blood pressure under the influence of an intravenous administration of the test compounds is illustrated. For comparision Saralasin is used. The data set forth in the Table 1 were obtained by calculating the average of the results of 6 experiments. The margins of error indicate the scatter of the main value.

Table 1

The influence of various angiotensin II analogs administered intravenously on the blood pressure, under i. v. infusion of angiotensin II

| Analog | Decrease in blood pressure (mmHg) after administration of | |
|---|---|---|
| | 10 μg/kg | 20 /μg/kg |
| | i.v. doses | |
| (Hydroxyacetyl$^1$,Leu$^8$)-AngII | −31 ± 4.7 | −42 ± 2.8 |
| (Hydroxyacetyl$^1$,Ile$^8$)-AngII | −24 ± 1.7 | −30 ± 2.3 |
| (Hydroxyacetyl$^1$,Thr(Me)$^8$)-AngII | −33 ± 5.3 | −38 ± 4.1 |
| (L-α-Hydroxypropionyl$^1$,Leu$^8$)-AngII | −32 ± 3.7 | −40 ± 2.7 |
| (1-α-Hydroxypropionyl$^1$,Ile$^8$)-AngII | −31 ± 3.3 | −38 ± 4.1 |
| Saralasin | −41 ± 2.5 | — |

From the data set forth in the above Table it can be clearly seen that every angiotensin II analogue substituted with a radical derived from an aliphatic-hydroxy-carboxylic acid in the 1-position possesses a significant blood-pressure-decreasing activity. The extent of the activity is proportional to the dose employed.

Tests were carried out also in the case of subcutaneous administration. It should be noted that this route of administration for angiotensin II or analogues thereof has not been published in the literature before. For subcutaneous administration a physiological saline solution containing the compound to be tested was supplemented with carboxymethylcellulose and gelatine, respectively. The results corresponding to the average of five separate tests are set forth in Table 2 below. The margins of error are related to the main value.

Table 2

The influence of various angiotensin II analoge administered subcutaneously on the blood pressure under i.v. infusion of angiotensin II

| Analogs | Dose μg/kg | Solvent | Decrease in blood pressure (mmHg) after | | | |
|---|---|---|---|---|---|---|
| | | | 15 | 30 | 60 | 120 |
| | | | minutes | | | |
| (L-α-Hydroxy-propyonyl, Leu$^8$)-Ang II | 200 | physiological salt solution CMC | −28 ± 3.1 | −38 ± 2.4 | −25 ± 1.5 | −5 ± 1.8 |
| (L-α-Hydroxy- | | | | | | |

Table 2-continued

The influence of various angiotensin II analoge administered subcutaneously on the blood pressure under i.v. infusion of angiotensin II

| Analogs | Dose μg/kg | Solvent | Decrease in blood pressure (mmHg) after | | | |
|---|---|---|---|---|---|---|
| | | | 15 | 30 | 60 | 120 |
| | | | minutes | | | |
| propyonyl,Ile$^8$)-Ang II | 200 | gelatine | −28 ± 10 | −28 ± 7.0 | −25 ± 6.0 | −5 ± 7.3 |

CMC = carboxymethylcellulose

According to the data given hereinabove the subcutaneously administered new compounds of this invention decrease the high blood pressure induced intentionally, in a significant manner, even 60 minutes after administration.

The term "complexes of the peptides according to the invention" is used herein to refer to complex compounds formed with certain organic materials, endowing the peptides with a delayed-action effect. Typical representatives of these organic compounds are gelatines, carboxymethylcelluloses, alginic acid esters, poly(fluoroethinephosphates), amino acid polymers or other polymers and copolymers.

The peptides according to the invention as well as pharmaceutically acceptable salts and complexes thereof are used for pharmacological purposes in the form of conventional pharmaceutical compositions. These pharmaceutical compositions contain the compounds according to the invention in admixture with organic or inorganic carriers suitable for enternal or parenteral administration. Thus pharmaceutical compositions may be formulated as solid lyophilizates, in which various inert compounds not reacting with peptides, e.g. hydrocarbons can be used as carriers. When the pharmaceutical compositions are formulated as dilute or concentrated suspensions or emulsions, they contain also various preserving and stabilizing agents.

Pharmaceutical compositions containing the compounds according to the invention may be used for differenciated detection of renal hypertension as well as for the treatment of every syndrome caused by an increased renal blood pressure.

Further details of the invention are illustrated by the following non-limiting Examples. The abbreviations used in the Examples correspond to those generally used in the literature (J. Biol. Chem. 247, 977 (1972)). The α-amino acids are designated by the syllable "0" put before the symbol corresponding to the amino acid in question. Thus for examples OGly stands for aminooxyacetic acid; OAla represents α-aminooxypropionic acid etc. Further abbreviations are for instance: PFP=pentafluorophenyl and Z=carbomethoxy.

During the process according to the invention evaporation is always carried out in Büchi Rotava or equipments. The melting points were determined in a Dr. Tottoli apparatus (made by Büchi). Thin layer chromatography was carried out on "Kleselgel G nach Stahl" silica gel plates (E. Merck, Darmstadt). The chromatograms were developed by the following solvent mixtures:

1. ethyl acetate: (20:6:11 mixture of pyridine/acetic acid/water)=95:5
2. ethyl acetate: (20:6:11 mixture of pyridine/acetic acid/water)=90:10
3. ethyl acetate: (20:6:11 mixture of pyridine/acetic acid/water)=80:20
4. ethyl acetate: (20:6:11 mixture of pyridine/acetic acid/water)=70:30
5. 4:1:5 mixture of n-butanol/acetic acid/water
6. 30:6:20:24 mixture of n-butanol/acetic acid/pyridine/water
7. 1:1:1:1 mixture of n-butanol/ethyl acetate/acetic acid/water In the Examples when indicating the $R_f$ values reference is made to the numbers of the above solvent systems.

Paper electrophoresis was accomplished in a LMIM, medium-voltage horizontal equipment, on an MN 214 paper, in a pH=1.9 buffer solution, beside glutaminic acid. Voltage: 450 V, time: 3 hours.

The thin layer chromatograms were developed partly with a ninhydrine solution, partly with a conventional chlorinating technique carried out with an o-tolidine-KJ solution.

The end product was purified as described below: 0.5 g. of a free peptide were thereafter dissolved in 4 ml. of a 0.01 n ammonium acetate buffer. The solution obtained was overlayered on a carboxymethyl cellulose (CMC 52) column of 0.5 lit. The column was previously brought into an equilibrium state with the buffer solution described above. 1.5 lit. of a 0.01 M ammonium acetate solution and 1.5 lit. of a 0.4 M ammonium acetate solution were admixed with a gradient stirrer and gradient elution was carried out. The flow velocity was adjusted to 25 ml./hour and 10-ml. fractions were collected. The eluate leaving the column was continuously registrated by means of an LKB Uvicord-II apparatus and on the basis of the curve obtained the main fractions were lyophilized in a Leybold-Hereus lyophilizing a apparatus. The lyophilizate prepared in this way was rechromatographed using the same gradient eluting technique and the eluate were lyophilized again.

EXAMPLE 1

(Hydroxyacetyl$^1$,Leu$^8$)-angiotensin II

Step I

Boc-Arg(NO$_2$)-Val-Tyr(Bzl)-Ile-His(Dnp)-Pro-Leu-ONB

To a solution of 4.2 g. (12 mmoles) of Leu-ONB . HBr in 5 M ml. of chloroform 1.68 ml. of triethyl amide and 3.81 g. (10 mmoles) of Boc-Pro-OPFP are added. The reaction mixture is stirred at room temperature for 20 minutes, shaken with water and subsequently with a 10% aqueous citric acid solution and dried. The chloroform solution is evaporated. The protected dipeptide ($R_f^1$=0.8) obtained is dissolved in 20 ml. of a 8 M solution of hydrochloric acid in dioxane. After 10 minutes the solution is diluted with dry ether and evaporated.

The dipeptide chlorohydrate prepared in this way ($R_f^4=0.56$) is dissolved in 50 ml. of chloroform, the pH-value of the solution is adjusted to 8 with triethyl amine and 8.8 g. (15 mmoles) of Boc-His(Dnp)-OPFP are added. The solution is stirred at room temperature for one hour taking care that the pH of the solution is kept at a value of 8. Thereafter 1.65 ml. of N,N-dimethyl-aminoethylamine are added to the solution to eliminate the excess active ester and after 10 minutes the reaction mixture is shaken with a 10% aqueous solution of citric acid, 1 N aqueous hydrochloric acid solution and a 5% aqueous sodium bicarbonate solution. Upon drying the solution is evaporated. The remaining protected tripeptide ($R_f^1=0.65$) is dissolved in 25 ml. of a 8 M solution of hydrochloric acid in dioxane and after 15 minutes the tripeptide ($R_f^4=0.47$) obtained is precipitated by adding dry ether. The precipitate is filtered off and is immediately dissolved in a mixture of 50 ml. of chloroform and 20 ml. of dimethylformamide. The pH-value is adjusted to 8 with triethylamine and 6.0 g. (15 mmoles) of Boc-Ile-OPFP are added. 30 minutes later the reaction mixture is evaporated to dryness and the residue is dissolved in 100 ml. of ethyl acetate. The ethyl acetate solution is extracted with an aqueous citric acid solution. 1 N aqueous hydrochloric acid solution and finally with water. Upon drying ethyl acetate is eliminated by evaporation and the residue treated with a 1:9 mixture of ether and n-hexane. The protected tripeptide obtained ($R_f^1=0.64$) is isolated and dissolved in 25 ml. of a 8 M solution of hydrochloric acid in dioxane. After 15 minutes the tetrapeptide ($R_f^4=0.40$) is precipitated with a dry ether and subsequently filtered off. Tetrapeptide chlorohydrate obtained is dissolved in a mixture of 50 ml. of chloroform and 30 ml. of dimethyl formamide and the pH-value of the solution is adjusted to 8 with triethyl amine. 6.0 g. (11.5 mmoles) of Boc-Tyr(Bzl)-OPFP are added. After 15 minutes the solution is evaporated, the residue is dissolved in ethyl acetate and 0.66 ml. of N,N-dimethyl-aminoethylamine are added. After 10 minutes standing the ethyl acetate solution is shaken with a 10% aqueous citric acid solution, with 1 N aqueous hydrochloric acid solution and finally with water, dried and evaporated. The evaporation residue is treated with dry ether and the protected pentapeptide ($R_f^2=0.8$) is isolated by filtration. The product is dissolved in 25 ml. of a 8 N solution of hydrochloric acid in dioxane and after 15 minutes pentapeptide ($R_f^4=0.8$) obtained is precipitated with dry ether, filtered and washed with ether. The precipitate is then immediately dissolved in 50 ml. of dimethyl formamide, the pH-value is adjusted to 8 with triethyl amine and 4.2 g. (11 moles) of Boc-Val OPFP are added. After stirring at room temperature for one hour the solution is evaporated, the residue is dissolved in chloroform and shaken with a 10% aqueous citric acid solution, then with an 1 N aqueous hydrochloric acid solution and finally with water. The solution is dried, evaporated and the residue is treated with ether. The protected hexapeptide obtained ($R_f^2=0.82$) is isolated by filtration. The product is dissolved in 25 ml. of a 8 N solution of hydrochloric acid in dioxane and after 15 minutes hexapeptide ($R_f^3=0.55$) is precipitated with dry ether, filtered and washed with ether. The hexapeptide is immediately dissolved in 50 ml. of dimethyl formamide, the pH-value is adjusted to 8 with triethyl amine and 4.8 g. (10 mmoles) of Boc-Arg(NO$_2$)-OPFP are added. After 30 minutes the solvent is replaced by chloroform and the solution is shaken with a 1 N aqueous hydrochloric acid solution and subsequently with water. The solution is dried, evaporated and the residue is treated with ethanol. The protected heptapeptide ($R_f^2=0.8$) is isolated to give 7.6 g. (53% calculated for the starting Boc-Pro-OPFP). Melting point: 192° to 195° C.

Step 2

Z-OGly-Arg(NO$_2$)-Val-Tyr(Bzl)-Ile-His(Dnp)-Pro-Leu-ONB 1.8 g. (1.25 mmoles) of Boc-Arg(NO$_2$)-Val-Tyr(Bzl)-Ilo-His(Dnp)-Pro-Leu-ONB are dissolved in 10 ml. of a 8 M solution of hydrochloric acid in dioxane. After 15 minutes the free heptapeptide chlorohydrate is precipitated with dry ether, filtered and washed with dry ether ($R_f^3=0.36$). The product is immediately dissolved in 20 ml. of dimethyl formamide, the pH-value is adjusted to 8 with triethyl amine and 0.9 g. (2.3 mmoles) of Z-OGly-OPFP are added. After 15 minutes solvent is replaced by chloroform, the solution is shaken with 1 N aqueous hydrochloric acid solution and water. After drying and evaporation the residue is treated with a 2:8 mixture of ethanol and ether, the product is isolated by filtration, 1.6 g. (85%) of the title compound are obtained. Melting point: 165° to 174° C. ($R_f^2=0.80$).

Step 3

Elimination of the protecting groups 1.6 g. (1.0 mmoles) of Z-OGly-Arg(NO$_2$)-Val-Tyr(Bzl)-Ile-His(Dnp)-Pro-Leu-ONB are dissolved in 5 ml. of dimethyl formamide and 3.5 ml. of 2-mercaptoethanol are added. The solution is stirred at room temperature for one hour. Thereafter dry ether is added to the mixture and the precipitated substance is filtered off, washed with two 10-ml. portions of ether and purified by precipitation from methanol-ether. 1.3 g. (95%) of Z-OGly-Arg(NO$_2$)-Val-Tyr(Bzl)-Ile-His-Pro-Leu-ONB are obtained, $R_f^2=0.2$.

The peptide obtained above is dissolved in 30 ml. of a 5:1:1 mixture of methanol, acetic acid and water. 0.5 g. of a 10% palladium on charcoal catalyst are added and hydrogen is bubbled through the vigorously stirred solution for 20 hours. Progress of the reaction is monitored by thin layer chromatography. When the reaction terminates catalyst is filtered off, washed with 20 ml. of a 5:1:1 mixture of methanol, acetic acid and water, and the solution is evaporated to dryness. The residue is dissolved in an ethanol/water mixture and evaporated more subsequent times to eliminate acetic acid. The peptide is then isolated by treating with dry ethanol and filtered off. 0.8 g. (67%) of hydroxyacetyl[1],Leu[8]/-angiotensin II are obtained. Purification is performed as given above. $R_f^5=0.41$; $R_f^6=0.59$; $R_f^7=0.60$; $E_{Glu}/pH=1.9/=0.98$. Amino acid analysis: Pro: 1.0/1/; Val: 1.01/1/; Ile: 1.02/1/; Arg: 1.01/1/; His: 1.0/1/; Leu: 1.02/1/; Tyr: 0.73/1/.

EXAMPLE 2

(L-α-hydroxypropionyl[1],Leu[8])-angiotensin II

Step 1

Z-OAla-Arg(NO$_2$)-Val-Tyr(Bzl)-Ile-His(Dnp)-Pro-Leu-OMB 1.8 g. (1.25 mmoles) of Boc-Arg(NO$_2$)-Val-Tyr-(Bzl)-Ile-His(Dnp)-Pro-Leu-ONB obtained in Step 1 of Example 1 are dissolved in 8 ml. of a 8 M solution of hydrochloric acid in dioxane. The free heptapeptide is precipitated from the solution with dry ether, thereafter is filtered off and washed with dry ether ($R_f^3=0.36$).

The compound is immediately dissolved in 20 ml. of dimethyl formamide, the pH-value is adjusted to 8 with triethyl amine and 0.93 g. (2.3 mmoles) of Z-OAla-OPFP are added. After 15 minutes the solvent is replaced by chloroform and the solution obtained is shaken with a 1 N aqueous hydrochloric acid solution and subsequently with water. The extract is dried and evaporated. The residue is treated with a 4:1 mixture of ethanol and ether to afford 1.75 g. (93%) of the title compound. Melting point: 164° to 172° C.; $R_f{}^2 = 0.85$.

Step 2

Elimination of the protecting groups 1.6 g. of Z-OAlal-Arg(NO$_2$)-Val-Tyr(Bzl)-Ile-His(Dnp)-Pro-Leu-ONP are dissolved in 5 ml. of dimethyl formamide, 3.5 ml. of 2-mercaptoethanol are added and the mixture is stirred for 1 hour at room temperature. Thereafter dry ether is added and the precipitate obtained is filtered off and purified by methanol-ether precipitation. 1.3 g. (92%) of Z-OAla-Arg(NO$_2$)-Val-Tyr(Bzl)-Ile-His-Pro-Leu-ONB are obtained; $R_f{}^2 = 0.27$. This peptide is dissolved in a 5:1:1 mixture of methanol, acetic acid and water, 0.5 g. of a 10% palladium on charcoal catalyst are added and hydrogen gas is bubbled through the solution for 20 hours, with vigorous stirring. The progress of the reaction is monitored by thin layer chromatography. When the reaction is completed the catalyst is filtered off, washed and the solution is evaporated to dryness. Dissolution of the residue in an ethanol/water mixture and evaporation are repeated several times. The residue is then treated with dry ethanol to give (L-α-hydroxypropyl$^1$-Leu$^8$)-angiotensin II. Yield: 0.65 g. (70%). The product obtained is purified as described above. $R_f{}^5 = 0.36$; $R_f{}^6 = 0.57$; $R_f{}^7 = 0.60$; $E_{Glu}(pH = 1.9) = 0.97$. Amino acid analysis: Pro: 0.98(1); Val: 1.0(1); Ile: 1.1(1); Arg: 1.0(1); His: 0.98(1); Leu: 0.98; Tyr: 0.56(1).

EXAMPLE 3

(Hydroxyacetyl$^1$,Ile$^8$)-angiotensin II

Step 1

Boc-Arg(NO$_2$)-Val-Tyr(Bzl)-Ile-His(Dnp)-Pro-Ile-ONB

To a solution of 4.15 g. (15 mmoles) of Ile-ONB.HCl in 50 ml. of chloroform 2.1 ml. of triethylamine and added followed by the addition of 3.81 g. (10 mmoles) of Boc-Pro-DPFP. The reaction mixture is stirred for 20 minutes at room temperature. It is then shaken with water and with a 10% aqueous citric acid solution, dried and evaporated. The protected dipeptide obtained ($R_f{}^1 = 0.9$) is dissolved in 20 ml. of a 8 M solution of hydrochloric acid in dioxane and, after 10 minutes, the reaction mixture is diluted with dry ether and evaporated. The free dipeptide hydrochloride ($R_f{}^4 = 0.44$) is dissolved in 30 ml. of chloroform, the pH-value is adjusted to 8 with triethyl amine and 8.8 g. (15 mmoles) of Boc-His(Dnp)-OPFP are added. After one hour 1.65 ml. of N,N-dimethyl-aminoethylamine are added to the reaction mixture, which is shaken after 15 minutes, with a 10% aqueous citric acid solution, with a 1 N aqueous hydrochloric acid solution and finally with water. The extract is dried and evaporated. The protected tripeptide ($R_f{}^1 = 0.50$) is dissolved in 20 ml. of a 8 N solution of hydrochloric acid in dioxane, without isolation. After 15 minutes tripeptide ($R_f{}^4 = 0.25$) is precipitated with dry ether, filtered and washed with dry ether. It is then immediately dissolved in a mixture of 50 ml. of chloroform and 20 ml. of dimethyl formamide. The pH-value of the solution obtained is adjusted to 8 with triethylamine and 6.0 g. (15 mmoles) of Boc-Ile-OPFP are added. The mixture is allowed to stand for 30 minutes, then the solvent is replaced by ethyl acetate and the solution is shaken with a 10% aqueous solution of citric acid, 1 N aqueous hydrochloric acid solution and finally with water. The extract obtained is dried, evaporated and the remaining protected tetrapeptide is isolated by extracting with a 9:1 mixture of n-hexane and ether. The protected tetrapeptide ($R_f{}^2 = 0.65$) is dissolved in 25 ml. of a 8 M solution of hydrochloric acid in dioxane. After 30 minutes the tetrapeptide obtained ($R_f{}^4 = 0.41$) is precipitated by addition of dry ether, filtered off and washed. It is immediately dissolved in 70 ml. of a 1:1 mixture of dimethyl formamide and chloroform. Whereafter the pH-value of the solution is adjusted to 8 and 6.0 g. (11.5 mmoles) of Boc-Tyr(Bzl)-OPFP are added. After 15 minutes the solvent is replaced by ethyl acetate and 0.66 ml. of N,N-dimethyl-aminoethylamine are added. After 15 minutes it is shaken with a 10% aqueous citric acid solution, 1 N aqueous hydrochloric acid solution and finally with water. After drying and evaporation the protected pentapeptide obtained ($R_f{}^2 = 0.59$) is isolated by adding dry ether. It is then dissolved in 20 ml. of hydrochloric acid in dioxane. After 15 minutes pentapeptide hydrochloride ($R_f{}^4 = 0.4$) is precipitated by adding dry ether, filtered and washed with 20 ml. of dry ether. It is immediately dissolved in 50 ml. of dimethyl formamide, the pH-value is adjusted to 8 with triethyl amine and 4.62 g. (12 mmoles) Boc-Val-OPFP are added. After one hour the solvent is replaced by chloroform and the solution is shaken with a 10% aqueous citric acid solution, 1 N aqueous hydrochloric acid solution and finally with water. The extract obtained is dried, evaporated and the evaporation residue is treated with dry ether to precipitate protected hexapeptide ($R_f{}^2 = 0.50$). It is then dissolved in 20 ml. of a 8 M solution of hydrochloric acid in dioxane and after 15 minutes from the solution obtained hexapeptide ($R_f{}^4 = 0.47$) is precipitated by adding dry ether. The hexapeptide is filtered off and washed with 20 ml. of dry ether. It is immediately dissolved in 50 ml. of dimethyl formamide, the pH value is adjusted to 8 with triethyl amine and 5.38 g. (12 mmoles) of Boc-Arg(NO$_2$)-OPFP are added. The mixture is allowed to stand for 30 minutes. Thereafter the solvent is replaced by chloroform and the solution is shaken with 1 N aqueous hydrochloric acid solution and water. The extract is dried, evaporated and the protected heptapeptide is isolated by means of ethanol. 9.7 g. (68% calculated for the starting Boc-Pro-OPFP) of the title compound are obtained. $R_f{}^2 = 0.67$.

Step 2

Z-OGly-Arg(NO$_2$)-Val-Arg(NO$_2$)-Val-Tyr(Bzl)-Ile-His(Dnp)-Pro-Ile-ONB are dissolved in 8 ml. of a 8 M solution of hydrochloric acid in dioxane. The solution is allowed to stand for 15 minutes, then the heptapeptide hydrochloride obtained ($R_f{}^4 = 0.45$) is precipitated with dry ether, filtered and washed with 20 ml. of dry ether. It is immediately dissolved in 10 ml. of dimethyl formamide, the pH value is adjusted to 8 with triethyl amine and 0.6 g. (1.5 mmoles) of Z-OGly-OPFP are added. After 30 minutes the solvent is replaced by chloroform and the solution is shaken with 1 N aqueous hydrochloric acid solution and water. The extract is dried and evaporated and the protected peptide is isolated with dry ether. 1.45 g. (85%) of the title compounds are obtained. Melting point: 151° to 158° C.; $R_f^2=0.68$.

Step 3

Elimination of the protecting groups 1.45 g. (0.94 mmoles) of Z-OGly-Arg(NO$_2$)-Val-Tyr(Bzl)-Ile-His(Dnp)-Pro-Ile-ONB are dissolved in 5 ml. of dimethyl formamide. 3.5 ml. of 2-mercapto ethanol are added, the solution is stirred for one hour and Z-OGly-Arg(NO$_2$)-Val-Tyr(Bzl)-Ile-His-Pro-Ile-ONB is precipitated with dry ether. After a methanol-ether precipitation 1.05 g. (82%) a peptide ($R_f^2=0.10$) are obtained. It is dissolved in 30 ml. of a 5:1:1 mixture of methanol, acetic acid and water, 0.5 g. of a 10% palladium on charcoal catalyst are added and hydrogen gas is bubbled through the vigorously stirred reaction mixture for 21 hours. The progress of the reaction is monitored by thin layer chromatography. The catalyst is filtered off, the solution is evaporated to dryness and the free peptide obtained is isolated with dry ethanol. 0.48 g. (64.5%) of (hydroxyacetyl$^1$,Ile$^8$)-angiotensin II are obtained. The product is purified in a manner known per se. $R_f^5=0.29$; $R_f^6=0.57$; $R_f^7=0.58$; $E_{Glu}(pH=1.9)=1.03$. Amino acid analysis: Pro: 0.99(1); Val: 1.15(1); Ile: 2.06(2); Tyr: 0.74(1); His: 0.98(1); Arg: 0.95.

EXAMPLE 4

(L-α-hydroxypropionyl$^1$,Ile$^8$)-angiotensin II

Step 1

Z-OAla-Arg(NO$_2$)-Val-Tyr(Bzl)-Ile-His(Dnp)-Pro-Ile-ONB 1.6 g. (1.1 mmoles) of Boc-Arg(NO$_2$)-Val-Tyr(Bzl)-Ile-His(Dnp)-Pro-Ile-ONB are dissolved in 8 ml. of a 8 M solution of hydrochloric acid in dioxane. The solution is allowed to stand for 15 minutes and the heptapeptide is precipitated by adding dry ether ($R_f^4=0.45$), filtered and washed. It is immediately dissolved in 10 ml. of dimethyl formamide, the pH-value is adjusted to 8 with triethyl amine and 0.61 g. (1.5 mmoles) of Z-OAla-OPFP are added. After 30 minutes the solvent is replaced by chloroform and the solution is shaken with a 1 N aqueous hydrochloric solution and water. After drying and evaporation the protected peptide obtained ($R_f^2=0.63$) is isolated with ether. 1.4 g. (83%) of the named compound are obtained. Melting point: 164° to 168° C.

Step 2

Elimination of the protecting groups 1.4 g. (0.9 mmoles) of Z-OAla-Arg(NO$_2$)-Val-Tyr(Bzl)-Ile-His(Dnp)-Pro-Ile-ONB are dissolved in 5 ml. of dimethyl formamide, and 3.5 ml. of 2-mercaptoethanol are added. The solution is allowed to stand for one hour and then Z-OAla-Arg(NO$_2$)-Val-Tyr(Bzl)-Ile-His-Pro-Ile-ONB is precipitated with ether and purified by methanol-ether precipitation. Yield: 0.8 (65%); $R_f^2=0.13$; $R_f^3=0.27$. The protected peptide obtained above is dissolved in 10 ml. of a 5:1:1 mixture of methanol, acetic acid and water. To the solution 0.5 g. of a 10% palladium on charcoal catalyst are added and hydrogen gas is bubbled through the mixture for 16 hours, with stirring. When the reaction terminates the catalyst is filtered off, the solution is evaporated and the product is isolated by means of dry ethanol. 0.4 g. (0.65%) of (L-α-hydroxy-propionyl$^1$-Ile$^8$)-angiotensin II are obtained. Purification is performed in a manner described above. $R_f^5=0.30$; $R_f^6=0.58$; $R_f^7=0.58$; $E_{Glu}(pH=1.9)=1.07$. Amino acid analysis: Pro: 1.04(1); Val: 0.98(1); Ile: 1.98(2); Tyr: 0.98(1); His: 1.05(1); Arg: 1.0(1).

EXAMPLE 5

(Hydroxyacetyl$^1$, Ala$^8$)-angiotensin II

Step 1

Boc-Arg(NO$_2$)-Val-Tyr(Bzl)-Ile-His(Dnp)-Pro-Ala-ONB

To a solution of 1.21 g. (4 mmoles) of Ala-ONB.HBr in 15 ml. of chloroform 0.56 ml. of triethyl amine and 0.76 g. (2 mmoles) of Boc-Pro-OPFP are added. The solution is stirred at room temperature for 20 minutes, extracted with water and a 10% aqueous citric acid solution, dried and evaporated. The protected dipeptide obtained ($H_f^1=0.64$) is dissolved in 4 ml. of a 8 M solution of hydrochloric acid in dioxane, without isolation. The solution is allowed to stand for 10 minutes, diluted with ether and evaporated. The dipeptide hydrochloride ($R_f^1=0.65$) is dissolved in 15 ml. of chloroform. The pH-value is adjusted to 8 with triethyl amine and 1.76 g. (3 mmoles) of Boc-His(Dnp)-OPFP are added. After 30 minutes 0.44 ml. of N,N-dimethylaminoethylamine are added to the solution. It is allowed to stand for 5 minutes, then shaken with a 10% aqueous citric acid solution, 1 N aqueous hydrochloric acid solution and 5% aqueous sodium bicarbonate solution. The extract is dried, evaporated and the protected tripeptide ($R_f^2=0.57$) is dissolved in 4 ml. of a 8 M solution of hydrochloric acid in dioxane. The tripeptide ($R_f^3=0.28$) is precipitated with dry ether after 10 minutes, filtered and washed with ether. It is immediately dissolved in 20 ml. of a 1:1 mixture of chloroform and dimethyl formamide. The pH-value is adjusted to 8 with triethyl amine and 1.58 g. (4 mmoles) of Boc-Ile-OPFP are added. After 20 minutes the solvent is replaced by ethyl acetate and the ethyl acetate solution is shaken with a 10% aqueous citric acid solution and subsequently with water. After drying and evaporation the protected tetrapeptide ($R_f^2=0.57$) is admixed with a 1:9 mixture of ether and n-hexane and filtered off. Thereafter it is dissolved in 4 ml: of a 8 M solution of hydrochloric acid in dioxane, allowed to stand for 15 minutes and tripeptide ($R_f^3=0.38$) is precipitated with dry ether, filtered off and washed. It is immediately dissolved in 15 ml. of a 2:1 mixture of chloroform and dimethyl formamide, the pH-value is adjusted to 8 with triethyl amine and 1.66 g. (3 mmoles) of Boc-Tyr(Bzl)-OPFP are added. After 15 minutes the solvent is replaced by ethyl acetate and 0.22 ml. of N,N-dimethyl aminoethylamine are added. Five minutes later it is shaken with a 10% aqueous citric acid solution, 1 N aqueous hydrochloric acid solution and finally with water. After drying and evaporation protected pentapeptide ($R_f^2=0.60$) is taken up in ether, filtered and washed with ether. Thereafter it is dissolved in 4 ml. of a 8 M solution of hydrochloric acid is dioxane. After 10 minutes pentapeptide ($R_f^4=0.62$) is precipitated with ether, filtered and washed with dry ether. It is immediately dissolved in 20 ml. of a 1:1 mixture of chloroform and dimethyl formamide, the pH value of the solution is adjusted to 8 with triethyl amine and 1.6 g. (4 mmoles) of Boc-Val-OPFP are added. The mixture is allowed to stand for 20 minutes. Thereafter solvent is replaced by ethyl acetate, the solution obtained is shaken with water and a 10% aqueous citric acid solution. The extract is dried, evaporated and the protected hexapeptide obtained ($R^2=0.65$) is taken up in ether, filtered and washed with ether. It is immediately dissolved in 20 ml. of dimethyl formamide, the pH value is adjusted to 8 with triethyl amine and 2.9 g. (6 mmoles) of Boc-Arg(NO$_2$)-OPFP are added. After 20 minutes the solvent is replaced by chloroform and the solution is shaken with a 10% aqueous citric acid solution and with water. After drying and evaporation the residue is triturated with a 1.2 mixture of ethyl acetate and ether, filtered and washed with the same solvent mixture. 2.0 g. (72%) of the corresponding protected heptapeptide are obtained. Melting point: 185° to 187° C.; $R_f^2=0.70$.

Step 2

Z-OGly-Arg(NO$_2$)-Val-Tyr(Bzl)-Ile-His(Dnp)-Pro-Aln-ONB 1.35 g. (1 mmole) of Boc-Arg(NO$_2$)-Val-Tyr(Bzl)-Ile-His(Dnp)-Pro-Ala-ONB are dissolved in 4 ml. of a 8 M solution of hydrochloric acid in dioxane. The solution is allowed to stand for 15 minutes, whereupon heptapeptide hydrochloride ($R_f^4=0.63$) is precipitated with dry ether, filtered and washed with ether. It is immediately dissolved in 15 ml. of dimethyl formamide, the pH value of the solution is adjusted to 8 with triethyl amine and 0.96 g. (2.5 mmoles) of Z-OGly-OPFP are added. After 20 minutes the solvent is replaced by chloroform and the solution is shaken with water. The aqueous extract is dried, evaporated and the protected peptide is isolated by treating with ethanol. Yield: 1.16 g. (83%); melting point: 133° to 135° C.; $R_f^2=0.72$.

Step 3

Elimination of the protecting groups 1.5 g. (1 mmole) of Z-OGly-Arg(NO$_2$)-Val-Tyr(Bzl)-Ile-His(Dnp)-Pro-Ala-ONB are dissolved in 5 ml. of dimethyl formamide and 2.95 ml. of 2-mercaptoethanol are added. The solution is allowed to stand for 1 hour, whereupon dry ether is added, the precipitate obtained is filtered off and washed with ethanol. 1.1 g. (82%) of Z-OGly-Arg(NO$_2$)-Val-Tyr(Bzl)-Ile-His-Pro-Ala-ONB is obtained. $R_f^2=0.15$; $R_f^3=0.40$. This protected peptide is dissolved in a 5:1:1 mixture of methanol, acetic acid and water, 0.5 g. of a 10% palladium on charcoal catalyst are added and hydrogen gas is bubbled through the mixture for 24 hours, with stirring. The progress of the reaction is monitored by thin layer chromatography. When the reaction terminates the catalyst is filtered off, washed with 15 ml. of a 5:1:1 mixture of methanol, acetic acid and water. The solution is then evaporated to dryness, the residue is taken up in an ethanol/water mixture and evaporated several times, then is isolated by means of dry ethanol. 0.55 g. (80%) of (hydroxyacetyl$^1$, Ala$^8$)-angiotensin II are obtained which are then purified as described above. $R_f^5=0.28$; $R_f^6=0.48$; $R_f^7=0.50$; $E_{Glu}(pH=1.9)=1.0$.

Amino acid analysis: Pro: 0.95(1), Ala: 1.1(1); Val: 1.0(1); Ile: 1.0(1); His: 1.0(1); Arg: 1.0(1); Tyr: 0.9(1).

EXAMPLE 6

(Hydroxyacetyl$^1$,Thr(Me)$^8$)-angiotensin II

Step 1

Boc-Arg(NO$_2$)-Val-Tyr(Bzl)-Ile-His(Dnp)-Pro-Thr(Me)-OMe 0.69 g. (3 mmoles) of Thr(Me)-OMe.HBr are dissolved in 30 ml. of chloroform, 0.42 ml. of triethylamine and 1.7 g. (4.5 mmoles) of Boc-Pro-OPFP are added. The solution is allowed to stand for two hours, whereupon 0.33 ml. of N,N-dimethylaminoethylamine are added. After 15 minutes the solvent is replaced by ethyl acetate and the solution obtained is shaken with a 10% aqueous citric acid solution, 1 N aqueous hydrochloric acid solution, water and finally with a 5% aqueous sodium bicarbonate solution. After drying and evaporation protected dipeptide ($R_f^1=0.76$) is dissolved in 2 ml. of a 8 M solution of hydrochloric acid in dioxane without isolation. After 15 minutes the solution is diluted with ether and evaporated. the residual dipeptide ($R_f^3=0.18$) is dissolved in 20 ml. of chloroform, the pH-value is adjusted to 8 with triethyl amine and 2.6 g. (4.5 mmoles) of Boc-His(Dnp)-OPFP are added. After stirring for 2 hours at room temperature 0.22 ml. of N,N-dimethylaminoethylamine are added to the solution, which is shaken after 15 minutes with a 10% aqueous citric acid solution, 1 N aqueous hydrochloric acid solution and with water. After drying and evaporation protected tripeptide ($R_f^1=0.5$) is dissolved in 4 ml. of a 8 N aqueous hydrochloric acid solution without previous isolation, and after 15 minutes tripeptide ($R_f^3=0.3$) is precipitated with dry ether, filtered and washed with ether. It is immediately dissolved in 20 ml. of a 1:1 mixture of chloroform and dimethyl formamide, the pH-value of the solution is adjusted to 8 with triethyl amine and 1.6 g. (5 mmoles) of Boc-Ile-OPFP are added. After 30 minutes the solvent is replaced by ethyl acetate and the ethyl acetate solution is shaken with a 10% aqueous citric acid solution, 1 N aqueous hydrochloric acid solution and finally with water. After drying and evaporation the residue is treated with a 1:9 mixture of ether and n-hexane, and thus the protected tetrapeptide is isolated. It is then dissolved in 7 ml. of a 8 M solution of hydrochloric acid in dioxane, the solution is allowed to stand for 15 minutes, whereupon tetrapeptide ($R_f^4=0.27$) is precipitated with dry ether. It is immediately dissolved in 20 ml. of a 1:1 mixture of chloroform and dimethyl formamide, the pH is adjusted to 8 with triethyl amine and 1.6 g. (3 mmoles) of Boc-Tyr(Bzl)-OPFP are added. After 30 minutes the solvent is replaced by ethyl acetate and 0.22 ml. of N,N-dimethylaminoethylamine are added. The solution is allowed to stand for 15 minutes, whereupon it is shaken with a 10% aqueous citric acid solution, 1 N aqueous hydrochloric acid solution and finally with water. The extract is dried and evaporated and the protected pentapeptide ($R_f^2=0.63$) is isolated by means of ether. 0.4 g. of the protected pentapeptide are obtained. The compound obtained is dissolved in 1 ml. of a 8 M solution of hydrochloric acid in dioxane and after 15 minutes pentapeptide ($R_f^4=0.47$) is precipitated with dry ether, filtered and washed with ether. It is immediately dissolved in 10 ml. of dimethyl formamide, the pH-value of the solution is adjusted to 8 with triethyl amine and 0.4 g. (1 mmole) of Boc-Val-OPFP are added. After one hour the solvent is replaced by chloroform and the solution obtained is shaken with a 10% aqueous citric acid solution. 1 N aqueous hydrochloric acid solution and water. After drying and evaporation the protected hexapeptide ($R_f^2=0.65$) is isolated by means of ether. Thereafter the product is dissolved in 1.5 ml. of a 8 M solution of hydrochloric acid in dioxane, the solution is allowed to stand for 15 minutes, whereupon hexapeptide ($R_f^4=0.48$) is precipitated with dry ether. The precipitate is filtered off, washed with ether and immediately dissolved in 10 ml. of dimethyl formamide. The pH-value of the solution is adjusted to 8 with triethyl amine and 0.45 g. (1 mmole) of Boc-Arg(NO$_2$)-OPFP are added. After one hour the solvent is replaced by ethyl acetate and the solution is shaken with a 10% aqueous citric acid solution, with a 1 N aqueous solution of hydrochloric acid and finally with water. The extract obtained is dried, evaporated and treated with a 9:1 mixture of ether and ethanol to give 0.45 g. (11.3%) of a protected heptapeptide. $R_f{}^2$=0.38; melting point: 199° to 203° C. (decomposition).

Step 2

Z-OGly-Arg(NO$_2$)-Val-Tyr(Bzl)-Ile-His(Dnp)-Pro-Thr(Me)-OMe 0.45 g. (0.34 mmoles) of Boc-Arg(NO$_2$)-Val-Tyr(Bzl)-Ile-His(Dnp)-Pro-Thr(Me)-OMe are dissolved in 2 ml. of a 8 M solution of hydrochloric acid in dioxane. The solution is allowed to stand for 15 minutes, whereupon heptapeptide is isolated by addition of dry ether ($R_f{}^4$=0.35). It is immediately dissolved in 10 ml. of dimethyl formamide, the pH value of the solution is adjusted to 8 with triethyl amine and 0.4 g. (1 mmole) of Z-Gly-OPFP are added. After one hour the reaction mixture is diluted with 30 ml. of chloroform and shaken with water. After drying and evaporation the protected peptide is isolated by means of a 9:1 mixture of ether and ethanol. Yield: 0.45 g. (93%); melting point: 158° to 162° C.; ($R_f{}^2$=0.44).

Step 3

Elimination of the protecting groups 0.45 g. (0.31 mmoles) of Z-OGLy-Arg(NO$_2$)-Val-Tyr(Bzl)-Ile-His(Dnp)-Pro-Thr(Me)-OMe are dissolved in 1.5 ml. of dimethyl formamide and 1 ml. of 2-mercaptoethanol are added. After one hour the substance is precipitated with dry ether, dissolved in methanol, decolored with a small amount of charcoal and finally evaporated. The evaporation residue is triturated with ether and filtered off. 0.38 g. (98%) of Z-OGly-Arg (NO$_2$)-Val-Tyr(Bzl)-Ile-His-Pro-Thr(Me)-OMe are obtained. $R_f{}^3$=0.16; $R_f{}^4$=0.52. The product is suspended in 5 ml. of dioxane and 1.2 ml. of a 1 N aqueous sodium hydroxide solution are added. The solution is allowed to stand for 1 hour, whereupon the pH-value thereof is adjusted to 3 with a 1 N aqueous hydrochloric acid solution. The precipitate obtained is dissolved in a 3:1 mixture of chloroform and dimethyl formamide. Upon drying and evaporation peptide free on the C-terminal end is treated with ether. 0.26 g. (70%) of free peptide are obtained; $R_f{}^4$=0.25. It is then dissolved in 10 ml. of a 5:1:1 mixture of methanol, acetic acid and water, 0.1 g. of palladium on charcoal catalyst are added and hydrogen gas is bubbled through the solution for 16 hours, with stirring. The progress of the reaction is monitored by thin layer chromatography. When the reaction terminates the catalyst is filtered off and the solution is evaporated to dryness. The residue is dissolved in a water/ethanol mixture and evaporated more subsequent times. 0.16 g. (80%) of (hydroxyacetyl[1], Thr(Me)-angiotensin II are obtained, which can be purified as described above. $R_f{}^5$=0.22; $R_f{}^6$=0.53; $R_f{}^7$=0.50; $E_{Glu}$(pH=1.9)=0.98. Amino acid analysis: Thr: 0.6(1); Val: 1.0(1); Ile: 1.02(1); Tyr: 0.85(1); His: 1.0(1); Arg: 0.96(1).

What we claim is:

1. A peptide of the formula:

X-Arg-Val-Tyr-Ile-His-Pro-Y wherein

X is hydroxyacetyl or α-hydroxypropionyl, and

Y is leucyl, isoleucyl, alanyl, or threonyl or an acid addition salt or a complex thereof.

2. A peptide as claimed in claim 1, which is hydroxyacetyl-Arg-Val-Tyr-Ile-His-Pro-Leu-OH and acid addition salts and complexes thereof.

3. A peptide as claimed in claim 1, which is α-hydroxypropionyl-Arg-Val-Tyr-Ile-His-Pro-Leu-OH and acid addition salts and complexes thereof.

4. A peptide as claimed in claim 1, which is hydroxyacetyl-Arg-Val-Tyr-Ile-His-Pro-Ile-OH and acid addition salts and complexes thereof.

5. A peptide as claimed in claim 1, which is α-hydroxypropionyl-Arg-Val-Tyr-Ile-His-Pro-Ile-OH and acid addition salts and complexes thereof.

6. A peptide as claimed in claim 1, which is hydroxyacetyl-Arg-Val-Tyr-Ile-His-Pro-Ala-OH and acid addition salts and complexes thereof.

7. A peptide as claimed in claim 1, which is hydroxyacetyl-Arg-Val-Tyr-Ile-His-Pro-Thr(Me)-OH and acid addition salts and complexes thereof.

* * * * *